United States Patent [19]

Campbell et al.

[11] Patent Number: 4,661,592

[45] Date of Patent: Apr. 28, 1987

[54] 4H-PYRIMIDO[2,1-A]ISOQUINOLIN-4-ONE DERIVATIVES

[75] Inventors: Arthur L. Campbell; Suzanne Evans Radak, both of Glenview, Ill.; Melanie J. Loots, Pennington, N.J.

[73] Assignee: G. D. Searle & Co., Skokie, Ill.

[21] Appl. No.: 625,061

[22] Filed: Jun. 27, 1984

[51] Int. Cl.$^4$ .................. C07D 471/04; A61K 31/505
[52] U.S. Cl. ..................................................... 544/252
[58] Field of Search ......................................... 544/252

[56] References Cited

U.S. PATENT DOCUMENTS 4,127,720 11/1978 Juby et al. ............................ 544/252
4,348,396 9/1982 Kierstead et al. ............... 544/252 X

FOREIGN PATENT DOCUMENTS 0143001 5/1985 European Pat. Off. ............ 544/252
0605940 10/1978 Switzerland ........................ 544/252

OTHER PUBLICATIONS

Tilley, et al., J. Med. Chem., vol. 26, No. 11, pp. 1638–1642 (1983).

*Primary Examiner*—Donald G. Daus
*Assistant Examiner*—Diana G. Rivers
*Attorney, Agent, or Firm*—Paul D. Matukaitis; Mary Jo Kanady; J. Timothy Keane

[57] ABSTRACT

This invention relates to a class of novel 4H-pyrimido[2,1-a]isoquinoline derivatives. The invention further relates to pharmaceutical compositions containing such 4H-pyrimido[2,1-a]isoquinoline-4-one derivatives and to the use of such compounds and compositions as anorectic agents. In particular, the novel 4H-pyrimido[2,1-a]isoquinoline-4-one derivatives are effective anorectic agents when administered orally.

7 Claims, No Drawings

4H-PYRIMIDO[2,1-A]ISOQUINOLIN-4-ONE DERIVATIVES

SUMMARY OF THE INVENTION

The present invention relates to a class of compounds of the formula

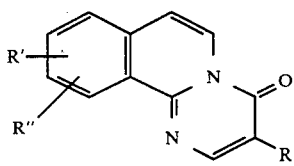
(I)

wherein
R is

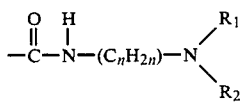

or $-(C_nH_{2n})-R_3$ wherein n is an integer of from 1 to 4; $R_1$ and $R_2$ are independently hydrogen or lower alkyl; and $R_3$ is a group selected from the class consisting of hydroxyl, amino, substituted amino, lower alkylcarboxyl, and

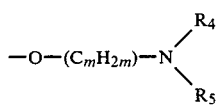

wherein m is an integer of from 1 to 4 and $R_4$ and $R_5$ are independently hydrogen or lower alkyl; and
R' and R" are independently hydrogen, halo, nitro or trifluoromethyl;
or pharmaceutically acceptable salts thereof when $R_3$ is amino, substituted amino or

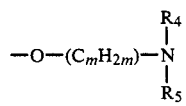

or when R is

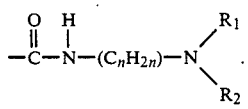

The invention further relates to pharmaceutical compositions containing the compounds of formula (I) and to the use of such compounds and compositions as anorectic agents.

DETAILED DESCRIPTION OF THE INVENTION

The term "lower alkyl" designates those alkyl radicals having straight or branched chains with a total of one to four carbons such as, for example, methyl, ethyl, propyl, isopropyl, butyl, isobutyl, and t-butyl.

As used herein, the term "substituted amino" refers to groups represented by the formula $-NR^6R^7$ wherein $R^6$ is lower alkyl and $R^7$ is hydrogen or lower alkyl. Illustrative of such substituted amino groups include, for example, methylamino, dimethylamino, ethylamino, di(isopropyl)amino, butylamino and the like.

The term "halo" encompasses fluoro, chloro, bromo and iodo.

As used herein, the term "lower alkylcarboxyl" refers to groups represented by the formula

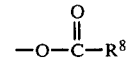

wherein $R^8$ is lower alkyl. Illustrative of such lower alkylcarboxyl groups include, for example, methylcarboxyl, ethylcarboxyl, isopropylcarboxyl, t-butylcarboxyl and the like.

The term "pharmaceutically acceptable salts" refers to salts derived from physiologically acceptable acids. Such physiologically acceptable acids include but are not limited to hydrochloric, hydroiodic, hydrobromic, phosphoric, sulphuric, toluenesulphonic, acetic, maleic, benzoic, citric, fumaric, gluconic, lactic, malic, nitric, saccharic, succinic, tartaric and the like.

A preferred embodiment of the present invention includes compounds of formula (I) wherein R' and R" are hydrogen. A more preferred embodiment includes compounds of formula (I) wherein R' and R" are hydrogen and R is $-(C_nH_{2n})-R_3$. It is most preferred that n is 1 and $R_3$ is hydroxyl, amino or lower alkylcarboxyl.

The compounds of the present invention may be prepared in accordance with one or more of the following procedures.

Compounds of formula (I) wherein R is $-(C_nH_{2n})-OH$ and n is and integer of from 2 to 4, may be prepared by reacting a trisdimethylaminomethane of the formula

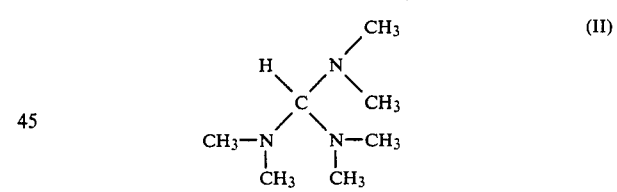
(II)

with a lactone of the formula

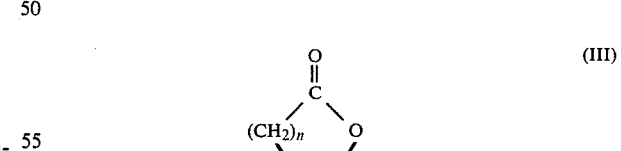
(III)

to yield an α-N,N-dimethylaminomethylenelactone of the formula

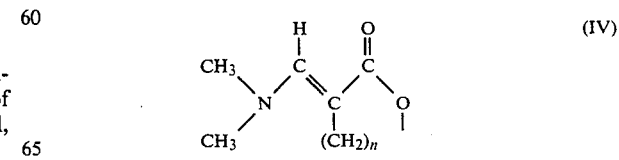
(IV)

The α-N,N-dimethylaminomethylenelactone is reacted with a 1-aminoisoquinoline of the formula

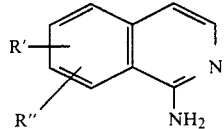

at a temperature of from 180° to 200° C. to yield the 3-(hydroxyalkyl)-4H-pyrimido[2,1a]isoquindin-4-one of the formula

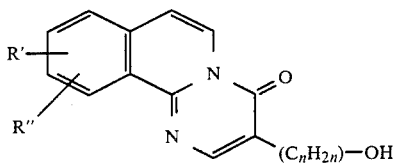

Preferably, to prepare compounds of the present invention wherein R is —CH$_2$OH, a pyrimido[2,1a]isoquinoline derivative of the formula

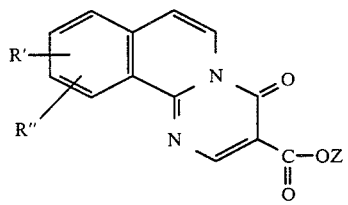

wherein Z is a cleavable ester group under nitrogen atmosphere in an appropriate solvent is reduced in the presence of an aluminum hydride at a temperature of from −70° to −25° C.

The compounds of formula (VII) may be prepared in accordance with the procedures described in U.S. Pat. No. 4,127,720.

The compounds of formula (I) wherein R is —(C$_n$H$_{2n}$)—R$_3$ and wherein R$_3$ is lower alkylcarboxy are prepared by reacting a compound of formula (VI) with an anhydride of the formula,

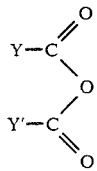

wherein Y and Y' are independently lower alkyl, in the presence of triethylamine to yield an ester of the formula

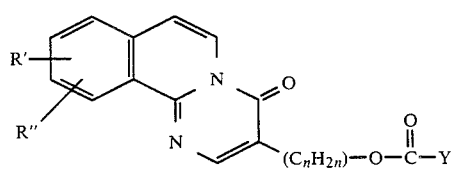

To prepare the compounds of the formula

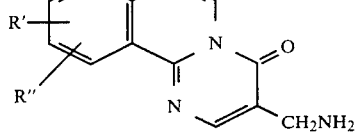

a 4-oxo-4H-pyrimido[2,1-a]isoquinoline-3-carbonitrile of the formula

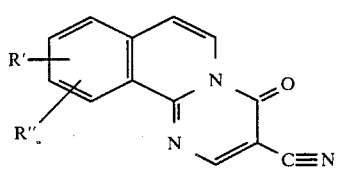

is hydrogenated under pressure in the presence of Raney nickel.

The compounds of the formula

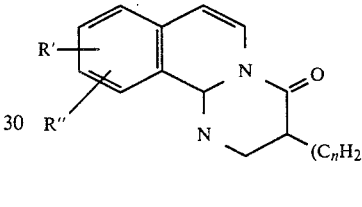

wherein n and m are independently integers of from 1 to 4, are prepared by reacting a 3-(hydroxyalkyl)-4H-pyrimido [2,1-a]isoquinolin-4-one of formula (VI) with an dialkyl aminoalkyl halide of the formula:

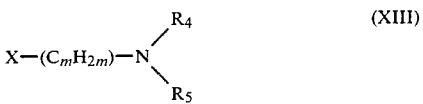

wherein X is halo and R$_4$ and R$_5$ are herein defined in the presence of sodium hydride.

To prepare compounds of the formula

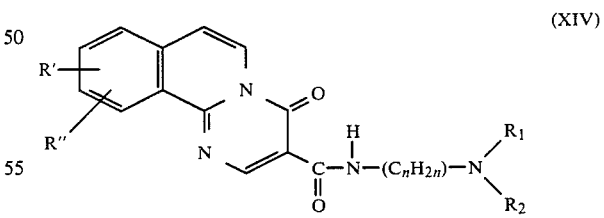

a pyrimido[2,1-a]isoquinolin-4-one derivative of formula (VII) is refluxed with an N$_1$,N$_1$-dialkylalkenediamine of the formula

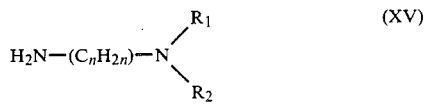

wherein R$_1$ and R$_2$ are above defined.

The pharmaceutically acceptable acid addition salts of the compounds of the present invention may be prepared by conventional procedures, e.g. by reacting the free base in a suitable solvent in which the free base is soluble, e.g. acetone or ethanol, with a solution containing one equivalent of the desired acid in a suitable solvent, e.g. dioxane or ethanol. The salt generally precipitates from solution or is recovered by evaporation of the solvent.

The compounds of the present invention are useful as anorectic agents. The anorectic utility of the compounds may be demonstrated by showing a dose responsive decrease in food intake and subsequent weight loss upon administration of the compounds to a subject.

The compounds of the present invention may be administered by any suitable route, preferably in the form of a pharmaceutical composition adapted to such route and in a dose effective for the treatment intended. Accordingly, the invention provides a class of novel pharmaceutical compositions comprising one or more compounds of the present invention in association with one or more non-toxic, pharmaceutically acceptable carriers and/or diluents and/or adjuvants and if desired other active ingredients. The composition is preferably administered orally.

For oral administration, the pharmaceutical composition may be in the form of, for example, a tablet, capsule, suspension or liquid. The pharmaceutical composition is preferably made in the form of a dosage unit, i.e., a tablet or capsule, containing a particular amount of the active ingredient. Such dosage units may contain from about 5 to 250 mg, preferably from about 25 to 150 mg, of the active ingredient. A suitable daily dose for a patient may vary widely depending on the condition of the patient and other factors. However, a dose of from about 0.1 to 300 mg/kg body weight, preferably from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg per kg body weight injected per day in multiple doses depending on the disease being treated. A preferred daily dose would be from about 1 to 30 mg/kg body weight per day.

As indicated, the appropriate dose adminstered and the treatment regimen will be dependent, for example, on the severity of the condition thereof, on the route of administration, on the patient being treated and his response to treatment, and therefore may be widely varied.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al., Remington's Pharmaceutical Sciences, 14th ed., Merck Publishing Co., Eaton, Pa., 1965.

The following examples describe in detail compounds illustrative of the present invention and methods which have been devised for their preparation. It will be apparent to those skilled in the art that many modifications, both of materials and of methods, may be practiced without departing from the purpose and intent of this disclosure.

EXAMPLE 1

To 12.0 g of ethyl 4-oxo-4H-pyrimido[2,1-a]isoquinoline-3-carboxylate (44.7 mmole) dissolved in 600 ml dry methylene chloride cooled to $-50°$ to $-70°$ C. under nitrogen was added dropwise over 15 minutes 92 ml of diisobutylaluminum hydride (1M in hexane, 92.0 mmole). The reaction mixture was stirred for 1 hour, then allowed to slowly warm to room temperature. After hydrolyzing in the cold ($-70°$ C.) with 40 ml of methanol the mixture was again allowed to warm to room temperature with stirring overnight, when the solids were separated by filtration and extracted with hot methanol. The filtrates were combined and concentrated in vacuo to give a crude product which was crystallized from chloroform/hexane. The crude product was dissolved in 300 ml of methanol, treated with decolorizing charcoal at reflux and filtered hot. The resulting solution was reduced to one-third initial volume. The solution was cooled to 25° C., ether was added and the resulting mixture was cooled to $-20°$ to $-50°$ C. until 3-(hydroxymethyl)-4H-pyrimido [2,1-a]isoquinolin-4-one crystallized as white needles (2.55 g, 28% yield) having the formula:

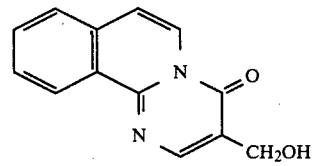

and a melting point of 198° C. and the following elemental analysis:

$C_{13}H_{10}N_2O_2$ (MW=226.23): Calculated: C, 69.02; H, 4.46; N, 12.38. Found: C, 68.88; H, 4.40; N, 12.36.

EXAMPLE 2

To 3.0 g of 3-(hydroxymethyl)-4H-pyrimido [2,1-a]isoquinolin-4-one (13.3 mmole) suspended in 100 ml chloroform with 10 ml of triethylamine and a trace of 4-dimethylaminopyridine was added 5.0 g of acetic anhydride (50.0 mmole). The reaction mixture was refluxed for 2 hours, then cooled to room temperature and washed twice with water. The organic layer was dried and concentrated in vacuo to give a crude solid which was crystallized from methylene chloride/hexane to yield 3-(hydroxymethyl)-4H-pyrimido[2,1-a]isoquinolin-4-one acetate as yellow crystals (2.09 g, 59% yield) of the formula:

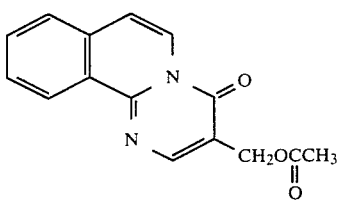

having a melting point of 173.3° C. and the following elemental analysis:

$C_{15}H_{12}N_2O_3$ (MW=268.27): Calculated: C, 67.15; H, 4.51; N, 10.44. Found: C, 66.98; H, 4.48; N, 10.39.

EXAMPLE 3

22.6 g of 4-oxo-4H-pyrimido[2,1-a]isoquinoline-3-carbonitrile (102.2 mmole) dissolved in 400 ml of THF and 52.8 g of ammonia was hydrogenated for 5 hours at a pressure of 60 psi at room temperature, using 2.26 g of Raney nickel as the catalyst. The solution was concentrated in vacuo to yield a residue which was suspended in methanol and treated with 25 ml. of isopropanolic hydrochloric acid solution to yield 6.37 g of a crude product as a light brown solid. 2.7 g of this solid was suspended in ethanol/methanol and treated with 20 ml. of isopropanolic hydrochloric acid solution while heating on a steam bath. Cooling and filtering afforded 3-(aminomethyl)-4H-pyrimido[2,1-a]isoquinolin-4-one, dihydrochloride (1.6 g; 28% yield) of the formula:

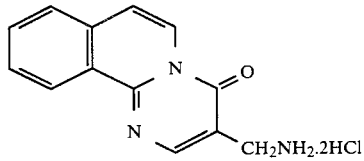

having a melting point of 291.1° C. and the following elemental analysis:

$C_{13}H_{11}N_3O.2HCl$ (MW=298.17): Calculated: C, 52.36; H, 4.39; N, 14.09; Cl, 23.78. Found: C, 52.02; H, 4.32; N, 13.86; Cl, 23.01.

EXAMPLE 4

To 0.7 g of sodium hydride (14.5 mmol) stirred in 40 ml of dry dimethylformamide under nitrogen was added dropwise over a 15 minute period a solution of 2.0 g of 3-(hydroxymethyl)-4H-pyrimido[2,1-a]isoquinolin-4-one (8.3 mmol) in 40 ml of warm dimethylformamide. After stirring for 1 hour, 1.58 g of diethylaminoethyl chloride (11.6 mmol) was added dropwise over a 15 minute period. The reaction mixture was stirred for 3 hours, then poured onto ice-water and extracted 3 times with 500 ml of methylene chloride. The extracts were dried and concentrated in vacuo to yield a semi-solid, to which 15 ml of isopropanolic hydrochloric acid solution and diethyl ether were added. The crystalline solid which formed was collected and washed with ether to yield 3-[[2-(diethylamino)ethoxy]methyl]-4H-pyrimido[2,1-a]isoquinolin-4-one dihydrochloride (0.973 g; 28% yield) of the formula:

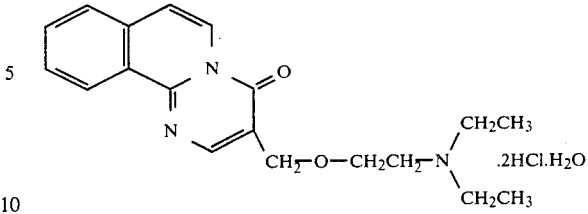

having a melting point of 128.7° C. and the following elemental analysis:

$C_{19}H_{23}N_3O_2.2HCl.H_2O$ (MW=416.34): Calculated: C, 54.81; H, 6.54; N, 10.09; Cl, 17.03. Found: C, 54.98; H, 6.96; N, 10.05; Cl, 16.88.

EXAMPLE 5

1.27 g of ethyl 4-oxo-4H-pyrimido[2,1-a]isoquinoline-3-carboxylate (4.73 mmol) and 4.1 ml of N,N-dimethylethylenediamine (3.13 g 35.5 mmol) were refluxed with stirring for 24 hours. The excess amine was then distilled off, yielding a beige solid which was dissolved in methylene chloride and filtered through silica gel. Concentration of the eluent in vacuo yielded 3-[(dimethylamino)methyleneiminocarbonyl]-4H-pyrimido[2,1-a]isoquinolin-4-one (1.137 g; 73% yield) of the formula:

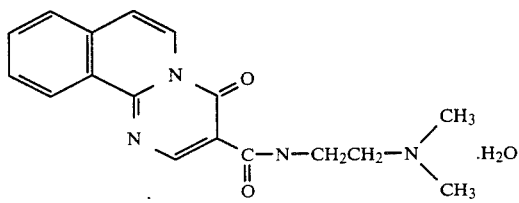

having a melting point of 162°-166° C. and the following elemental analysis:

$C_{17}H_{18}N_4O_2.H_2O$ (MW=328.37): Calculated: C, 62.17; H, 6.14; N, 17.06. Found: C, 62.24; H, 6.33; N, 17.88.

EXAMPLE 6

A heterogenous mixture containing 14.4 g of 1-isoquinolinamine (0.1 m) and 14.12 g of dihydro-3-[(dimethylamino)methylene]-2(3H)-furanone was heated to 200° C. for 4 hours to yield a homogenous yellow orange solution which solidified upon cooling to ambient temperature. The solidified reaction mixture was titurated with methanol and ethyl acetate to yield 3-(2-hydroxyethyl)-4H-pyrimido[2,1-a]isoquinolin-4-one as a tan solid (18.0 g; 75% yield) of the formula

having a melting point of 185.2°-187.0° C. and the following elemental analysis:

$C_{14}H_{12}N_2O_2$ (MW=240.25): Calculated: C, 69.98; H, 5.04; N, 11.66. Found: C, 69.87; H, 5.00; N, 11.52.

EXAMPLE 7

Male Sprague-Dawley derived rats, Charles River Breeders (Portage, MI), weighing between 200–400 grams at the time of testing, were employed in the food intake studies and water intake studies. The rats were housed individually and kept on a 12 hour light-dark-light cycle. The room temperature ranged between 23°–25° C.

Food Intake Studies

The rats employed in food intake testing were food deprived on the day preceding testing and were divided into experimental groups that were matched on the basis of average daily food intake and body weight. At approximately 24 hour post-deprivation, the rats were administered a test sample containing as the active ingredient a compound of the present invention. All test samples employed herein were prepared and homogenized in a vehicle of normal saline (to which a few drops of PG/Tween 80 was added). The test samples were administered at an injection volume of 2 ml/kg, unless otherwise stated. Thirty minutes following administration of the test samples, pre-weighed food jars containing ground meal were placed in the rats' cages. (Prior to testing the rats were given ground meal for a minimum of 3 days to familiarize the rats with this food.) After 1, 2 and 6 hours of food access, the jars were removed, weighed and returned to the rats' cages providing a 1, 2 and 6 hours intake measurement. Controls were simultaneously run in accordance with the above procedures except that the test samples administered to the control rats did not contain any active ingredient. The results obtained are represented in Table I as a percent of control values. A student t test was used for making statistical comparisons, and the p-values are based upon two-tailed comparisons. The compound employed as the active ingredient on the test sample is indicated by the example number which describes its preparation.

TABLE I

| | Food Intake Test Results | | | | |
|---|---|---|---|---|---|
| Active Ingredient | Dose & Route | n | 1 Hr. | 2 Hr. | 6 Hr. |
| | | | | Food Intake % of control | |
| Example 1 | 32.0 mg/kg i.g. | 12 | 61.8[1] | 77.4[3] | 90.4 |
| Example 2 | 32.0 mg/kg i.g. | 12 | 51.4[1] | 67.1[2] | 89.8 |
| Example 3 | 32.0 mg/kg i.g. | 12 | 51.3[1] | 71.4[2] | 92.3 |
| Example 4 | 32.0 mg/kg i.g. | 9 | 70.8[3] | 80.8 | 90.9 |
| Example 5 | 32.0 mg/kg i.g. | 12 | 82.4[2] | 87.5 | 88.3 |

[1] $p < .01$ compared with saline control
[2] $p < .05$ compared with saline control
[3] $.05 < p < .09$ compared with saline control The above results indicate that certain compounds of the present invention are effective anorectic agents. In addition, compounds of the present invention possess oral appetite suppressant activity. Furthermore, in addition to the above illustrated anorectic activity, the compounds of the present invention also possess other pharmaceutical activity, such as for example, the compounds are benzodiazepine antagonists.

Although this invention has been described with respect to specific modification, the details thereof are not to be construed as limitations, for it will be apparent that various equivalents, changes and modification may be resorted to without departing from the spirit and scope thereof and it is understood that such equivalent embodiments are intended to be included therein.

What is claimed is:

1. A compound of the formula

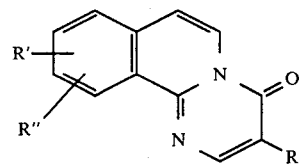

wherein R is

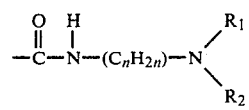

or $-(C_n-H_{2n})-R_3$ wherein n is an integer of from 1 to 4; $R_1$ and $R_2$ are independently hydrogen or lower alkyl; and $R_3$ is a group selected from the class consisting of hydroxyl, amino, substituted amino which is represented by the formula $-NR^6R^7$ wherein $R^6$ is lower alkyl and $R^7$ is hydrogen or lower alkyl, lower alkylcarboxyl which is represented by the formula

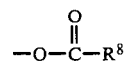

wherein $R^8$ is lower alkyl, and

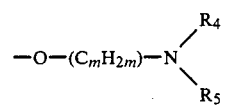

wherein m is an integer of from 1 to 4 and $R_4$ and $R_5$ are idependently hydrogen or lower alkyl; and R' and R'' are independently hydrogen, halo or trifluoromethyl; or pharmaceutically acceptable salts thereof when $R_3$ is amino substituted amino or

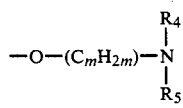

or when R is

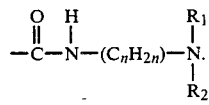

2. A compound according to claim 1 wherein R is a $-(C_nH_{2n})-R_3$ group and $R_3$ is hydroxyl, amino or alkylcarboxy.

3. A compound according to claim 2 wherein n is 1.

4. A compound according to claim 3 wherein R' and R'' are hydrogen.

5. A compound according to claim 4 wherein the compound is 3-(hydroxymethyl)-4H-pyrimido[2,1-a]isoquinolin-4-one acetate.

6. A compound according to claim 4 wherein the compound is 3-(aminomethyl)-4H-pyrimido[2,1-a]isoquinolin-4-one dihydrochloride.

7. A compound according to claim 4 wherein the compound is 3-(hydroxymethyl)-4H-pyrimido[2,1-a]isoquinolin-4-one.

* * * * *

UNITED STATES PATENT AND TRADEMARK OFFICE
CERTIFICATE OF CORRECTION

PATENT NO. : 4,661,592
DATED : April 28, 1987
INVENTOR(S) : Campbell et al.

It is certified that error appears in the above-identified patent and that said Letters Patent are hereby corrected as shown below:

Column 3, line 10, reading "[2,1a]" should read -- [2,1-a] --.

Column 3, lines 22 and 23, reading "[2-,1a]" should read -- [2,1-a] --.

Column 7, line 45, reading "$C_{13}H_{11}N_3O.2HCl$" should read -- $C_{13}H_{11}N_3O \cdot 2HCl$ --.

The first formula in Column 8, that portion of the formula reading ".2HCl.H$_2$O" should read -- $\cdot 2HCl \cdot H_2O$ --.

Column 8, line 14, reading "$C_{19}H_{23}N_3O_2.2HCl.H_2O$" should read -- $C_{19}H_{23}N_3O_2 \cdot 2HCl \cdot H_2O$ --.

The second formula in Column 8, that portion of the formula reading ".H$_2$O" should read -- $\cdot H_2O$ --.

Column 8, line 42, reading "$C_{17}H_{18}N_4O_2.H_2O$" should read -- $C_{17}H_{18}N_4O_2 \cdot H_2O$ --.

The first footnote for Table I in Column 9, reading "[1]p" should read -- 1:p --.

The second footnote for Table I in Column 9, reading "[2]p" should read -- 2:p --.

The third footnote for Table I in Column 9, reading "[3].05" should read -- 3:.05 --.

UNITED STATES PATENT OFFICE
CERTIFICATE OF CORRECTION

PATENT NO. : 4,661,592

DATED : April 28, 1987

INVENTOR(S) : Campbell et al.

It is certified that error appears in the above—identified patent and that said Letters Patent are hereby corrected as shown below:

Column 10, line 50, reading "-N." should read -- -N --.

Signed and Sealed this

Twenty-third Day of August, 1988

Attest:

DONALD J. QUIGG

*Attesting Officer*   *Commissioner of Patents and Trademarks*